United States Patent [19]

Kroll et al.

[11] Patent Number: 4,769,760
[45] Date of Patent: Sep. 6, 1988

[54] TERRAIN BIASED DYNAMIC MULTIPLE THRESHOLD SYNCHRONIZATION METHOD AND APPARATUS

[75] Inventors: Mark W. Kroll, Minnetonka; Mark R. Pommrehn, Eden Prairie, both of Minn.

[73] Assignee: Cherne Medical, Inc., Minneapolis, Minn.

[21] Appl. No.: 25,523

[22] Filed: Mar. 13, 1987

[51] Int. Cl.⁴ .................... G06F 15/31; H04L 7/00
[52] U.S. Cl. ...................... 364/487; 128/712; 307/527; 324/78 F; 340/825.2; 364/413.06; 364/575; 375/118
[58] Field of Search ............... 364/417, 487, 574, 575; 340/825.20; 307/520, 527; 324/78 F; 128/670, 703, 710, 712; 328/63; 375/118

[56] References Cited

U.S. PATENT DOCUMENTS

| | | | |
|---|---|---|---|
| 3,713,029 | 1/1973 | Uchida | 328/63 |
| 3,759,248 | 9/1973 | Valiquette | 128/703 |
| 3,967,170 | 6/1976 | MacDonald et al. | 318/85 |
| 3,989,897 | 11/1976 | Carver | 179/1 P |
| 4,086,651 | 4/1978 | Muir et al. | 364/487 |
| 4,183,087 | 1/1980 | Huelsman | 364/487 |
| 4,192,003 | 3/1980 | Brock et al. | 364/574 |
| 4,223,681 | 9/1980 | Sherman | 364/575 |
| 4,241,312 | 12/1980 | Barnes et al. | 329/50 |
| 4,320,516 | 3/1982 | Kammerlander | 375/118 |
| 4,320,526 | 3/1982 | Gitlin | 375/118 |
| 4,352,094 | 9/1982 | Reneric | 364/575 |
| 4,412,299 | 10/1983 | Huffman | 375/118 |
| 4,494,242 | 1/1985 | Ehrenbard et al. | 375/118 |
| 4,495,585 | 1/1985 | Buckley | 364/487 |
| 4,514,855 | 4/1985 | Lang et al. | 375/118 |
| 4,537,202 | 8/1985 | Mancini et al. | 128/712 |
| 4,630,204 | 12/1986 | Mortara | 364/417 |
| 4,680,708 | 7/1987 | Ambos et al. | 364/417 |
| 4,694,402 | 9/1987 | McEachern et al. | 364/487 |

*Primary Examiner*—Parshotam S. Lall
*Assistant Examiner*—Kevin J. Teska
*Attorney, Agent, or Firm*—Anthony G. Eggink

[57] ABSTRACT

The method and device of the present invention is for synchronizing periodic signals. The method is comprised of the steps of obtaining input signals to be synchronized, delineating a plurality of terrain biased, dynamic threshold points, detecting the time at whcih each threshold point was attained by each input signal, averaging the times to determine a mean alignment time and aligning all signals with respect to the mean alignment time. The device of the present invention is comprised of an input system for receiving and converting an analog signal to a digital signal or signals; a microprocessor connected to the input system and having a control section for processing the signal in accordance with the method of the invention; and an output system connected to the microprocessor for sending the synchronized signal.

21 Claims, 5 Drawing Sheets

TERRAIN BIASED DYNAMIC MULTIPLE THRESHOLD SYNCHRONIZATION METHOD AND APPARATUS

BACKGROUND OF THE INVENTION

This invention relates to the synchronization of periodic electrical signals and, more particularly, to the enhanced resolution of periodic electrical signals by synchronization and computer averaging. This invention is particularly useful for minimizing the effects of noise in electrocardiographic signals.

Many electronic devices utilize electrical, acoustical and/or electromagnetic signals that remain constant or vary in a specified manner. For example, electronic measurement devices, such as medical diagnostic apparatus, detect signals related to the physical variables of the system or its components being monitored. Some such devices also utilize transmitted signals in the measurement process. Also, electronic communication devices transmit and receive electromagnetic signals to and from locations where the information contained in the signals is to be utilized.

These devices frequently experience undesired disturbances within their useful frequency band. Such disturbances are commonly referred to as noise which denotes any unwanted fluctuations in the signal characteristics that are desired or expected to remain constant or to vary in a specified manner. Generally, noise results from either sources outside a circuit, in which case it is called interference, or from random or accidental fluctuations in the circuit itself due to motion of the current carrier. Since electronic noise is, by definition, an unwanted disturbance, its reduction in communication and measurement circuitry, as well as other types of circuitry, is a constant aim for both hardware and software engineers.

Two major classifications of noise exist with respect to signals. The first, additive noise, is a relatively uniform disturbance which is present throughout the entire signal. Types of additive noise include Johnson noise and shot noise. Johnson noise or thermal noise is the noise produced by thermal agitation of charges in a conductor. It is random and has a uniform energy versus frequency distribution. Johnson noise is random in that it contains no periodic components and its future value is completely unpredictable. Shot noise is also random and is exhibited by fluctuations of current output average value resulting from random emissions of electrons. Johnson and shot noise are both white, in that they have a constant energy per unit band width that is independent of the central frequency of the band. The second type, multiplicative noise, is not uniformly present throughout the entire signal but may recur at regular intervals. It is not a truly random noise. An example of multiplicative noise is that occurring in an electrocardiographic signal due to patient movement. Such noise is exhibited, for example, in recurrent amplitude fluctuations in the cycles of the ECG signal.

Electronic measurement devices are often utilized in the medical field to detect, display and analyze periodic or cyclical bio-electric and bio-acoustic signals emanating from a patient's body. These devices may passively receive only one type of signal or simultaneously receive heterogeneous types of signals, for example, electrocardiographic, phonocardiographic, radio emissive and NMR image signals. Reception of such signals may be made at one or multiple locations. Still other devices are utilized in the medical field to synchronize an actively transmitted signal such as ultrasound with a received signal for either diagnostic or therapeutic purposes. These electro-medical measurement devices have often incorporated hardware and/or software components to reduce the noise level in the signals.

One known method of noise reduction utilizes a computer to repeatedly average a plurality of recurrent signal cycles to yield a composite signal which is then displayed for operator diagnosis or further analyzed by other means. In the process of averaging, however, the noise components of each signal cycle are attenuated because they are weaker than the components desired for medical purposes.

Computer averaging of an electrocardiographic signal or other periodic electrical signals requires the alignment or synchronization of each signal cycle with respect to a fixed reference point so that an accurate comparison of corresponding portions or data points of the cycles may be made. The reference point is typically established in the time domain. In the past, synchronization of periodic signals with respect to a time reference was accomplished by establishing a single, fixed threshold voltage level, the attainment of which by each successive signal cycle provided a reference time coordinate for alignment purposes.

However, a problem exists in computer averaging because the signal noise sought to be mitigated by the averaging technique interferes with the synchronization technique. Specifically, additive noise in the threshold voltage portion of the cycle causes uncertainties in the determination of a reliable reference time coordinate from which to base alignment. And, improperly aligned signals greatly diminish the reliability of the averaged signal. Additionally, multiplicative noise can cause the failure of the determination of an alignment reference in some cycles. Without an alignment reference, these cycles are not synchronized, which results in further distortion of the averaged signal.

Yet another problem exists with regard to the synchronization of signals. Direct current (DC) shifts in an electrical circuit can cause the baseline to fluctuate or wander. The baseline or terrain of a signal is a region of least absolute value voltage or amplitude. The baseline corresponds to an area of inactivity or of least activity in the underlying physical phenomena represented by the signal. The baseline voltage may either be constant over a period in which case it is isoelectric or it may be variable. Baseline wandering results in inconsistent cycle amplitudes which do not realistically depict changes in the underlying physical phenomena that the signal represents. The resulting deceptive representation of such phenomena may lead to erroneous synchronization. DC shifts are caused, for example, by a loose electrode or by patient movement during the monitoring of electrocardiographic signals.

Despite the need for an effective method and apparatus for synchronizing noisy signals having wandering baselines for subsequent computer averaging, none insofar as is known has been proposed or developed. And, more generally, despite the need for an effective, general purpose method and apparatus for synchronizing signals having additive noise, multiplicative noise and/or DC shifts, none insofar as is known has been proposed or developed.

Accordingly, an object of the present invention is to provide a method and apparatus for establishing accurate reference points for waveforms having additive noise so that they may be synchronized with respect to time. It is another object of this invention to provide a method and apparatus for establishing accurate reference points for waveforms having multiplicative noise and varying amplitudes so that they may be aligned with respect to time. A further object of this invention is to provide a method and apparatus for establishing an accurate reference points for aligning signals or recurrent cycles of a periodic signal having a wandering baseline. It is a particular object of the invention to provide a method and apparatus for accurately synchronizing a periodic signal for its subsequent averaging to reduce noise. Finally, and more particularly, it is an object of the invention to provide an improved synchronization method and apparatus for computer averaging of electrocardiographic signals.

SUMMARY OF THE INVENTION

The method and apparatus of the present invention is for synchronizing signals used in electronic signal analysis, display, or transmission devices. The method is comprised of the steps of detecting a signal, selecting a plurality of thresholds generally corresponding to the signal, detecting the time at which each said threshold is attained by the signal, and calculating the mean time at which the thresholds are attained by the signal. The mean time is used to synchronize the signal with other signals. The thresholds are preferably selected as percentages of the peak amplitude of the signal. The method additionally and preferably comprises the steps of determining the actual baseline of the signal and adding the baseline to each threshold to adjust them for DC shifts prior to detecting time attainment. These steps are repeatable for a plurality of input signals or for a plurality of successive cycles of an input periodic signal.

The method provides an accurate reference point for synchronizing input signals. The method eliminates uncertainties in the alignment of signals, with respect to time, for subsequent processing or display. This method, used in conjunction with computer averaging, is particularly provided for reducing noise in electrocardiographic or other signals which typically show DC shift or which have high amounts of additive and multiplicative noise.

The device for synchronizing periodic electrical signals comprises an input system for receiving and converting an analog signal to a digital signal or signals; a microprocessor connected to the input system and having a control section for processing the signal in accordance with the method of the invention; and an output system connected to the microprocessor for sending the synchronized signal. The control section further comprises means for selecting a plurality of terrain biased, dynamic threshold voltages which generally correspond to signal of interest; means for comparing signals with the threshold voltages and for detecting the times at which the threshold voltages are attained by the signals; means for determining the average threshold times for the signals; and means for aligning signals based on the average threshold times.

The device provides a means of establishing an accurate time reference for synchronizing input signals. The device reduces the deleterious effects of signal noise in establishing a precise time coordinate for synchronizing the signal for subsequent display, analysis, or transmission.

These and other benefits of this invention will become clear from the following description, by reference to the drawings.

DESCRIPTION OF THE PREFERRED EMBODIMENTS

Figure 1:
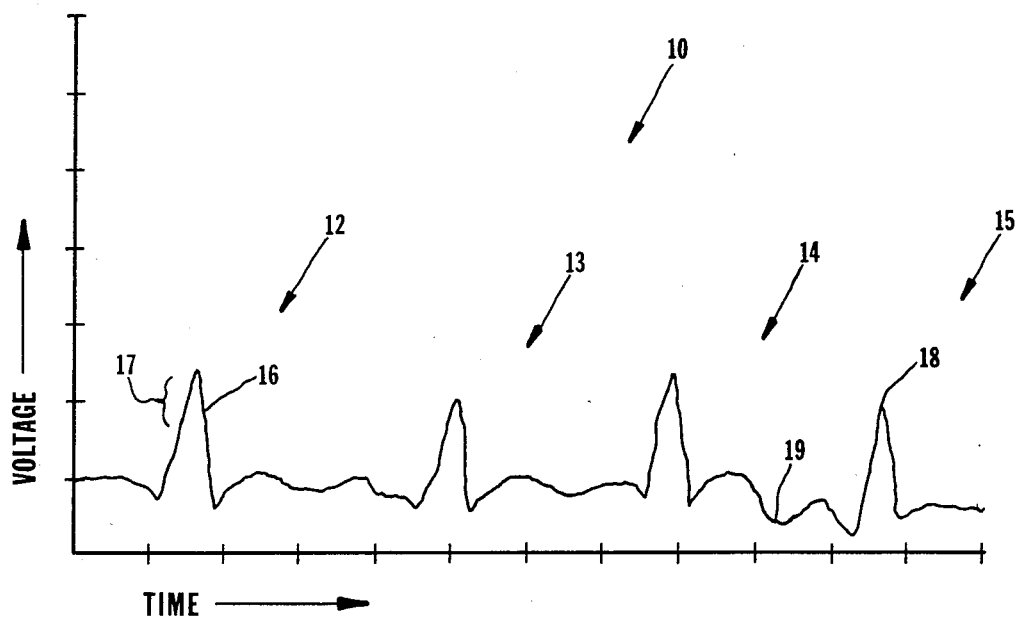
FIG. 1 is a standard human electrocardiographic trace exhibiting a periodic signal having a high noise level, both additive and multiplicative, and a wandering baseline.
Figure 2:
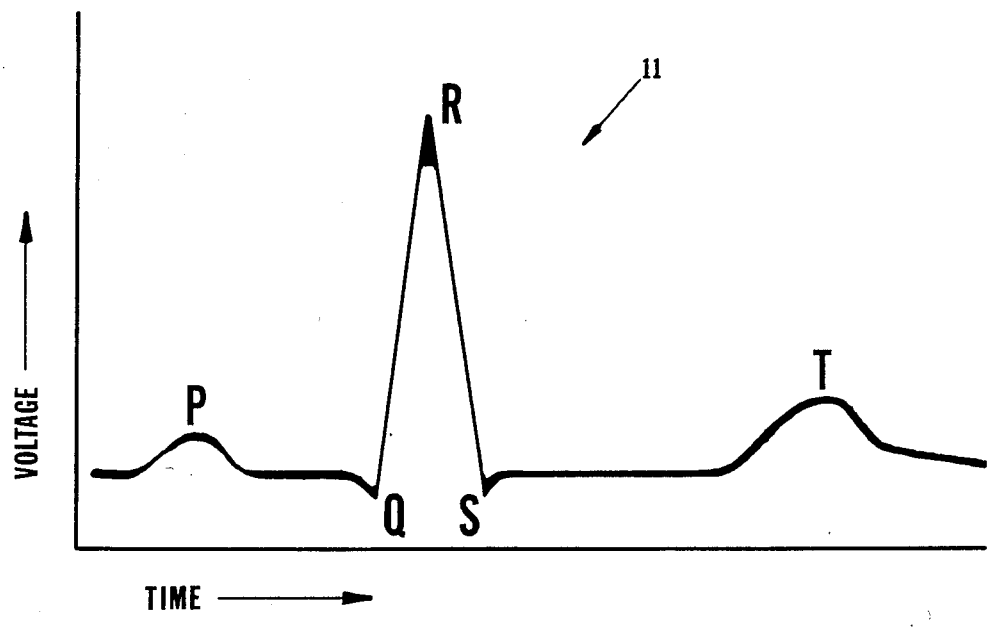
FIG. 2 is a composite, averaged electrocardiographic waveform which shows the P, R and T-waves as well as the QRS-complex.

The method of the present invention may be better understood by reference to FIGS. 1 and 2, which show examples of an electrocardiographic (ECG) signal. Other types of electrical, acoustic and/or electromagnetic signals, including non-periodic signals, may also be synchronized utilizing the teachings of this invention. The waveform 10 shown in FIG. 1 is that of a standard human periodic ECG signal. The waveform 10 shows a plurality of recurring electrical heart activity cycles or periods 12, 13, 14 and 15. Each cycle shown has a high amount of 60 Hz and white noise components which are normally present due to the ECG device circuitry or to outside interference. These noise components interfere with diagnostic analysis of cardiac activity components of the wave 10 by medical personnel or electro-medical devices and result in a low signal to noise voltage ratio (S/N). Averaging a plurality of these cycles yields a composite waveform 11, shown in FIG. 2. The composite signal 11 has a much lower noise level which allows for easier visualization of the true electrical heart activity which is of interest to the diagnostitian, including, among other things, the QRS-complex, the R-wave height and the ST-segment length. Additionally, the averaged signal 11 is more accurately analyzed by other electro-medical devices.

Signal averaging is commonly executed by means of a computer. Computer averaging requires aligning or synchronizing the cycles 12, 13, 14 and 15 with respect to a common reference point so that an accurate averaging of corresponding data points on the cycles is made. Such alignment is typically made with respect to a time coordinate. Time alignment is accomplished by establishing an alignment or synchronization reference time for each cycle. It is critical that the alignment time be accurately established with respect to the phase of the underlying signal 10. Errors in establishing the alignment time directly lead to misalignment of the signal cycles 12, 13, 14 and 15, which greatly reduces the reliability of subsequent signal averaging.

Figure 3:
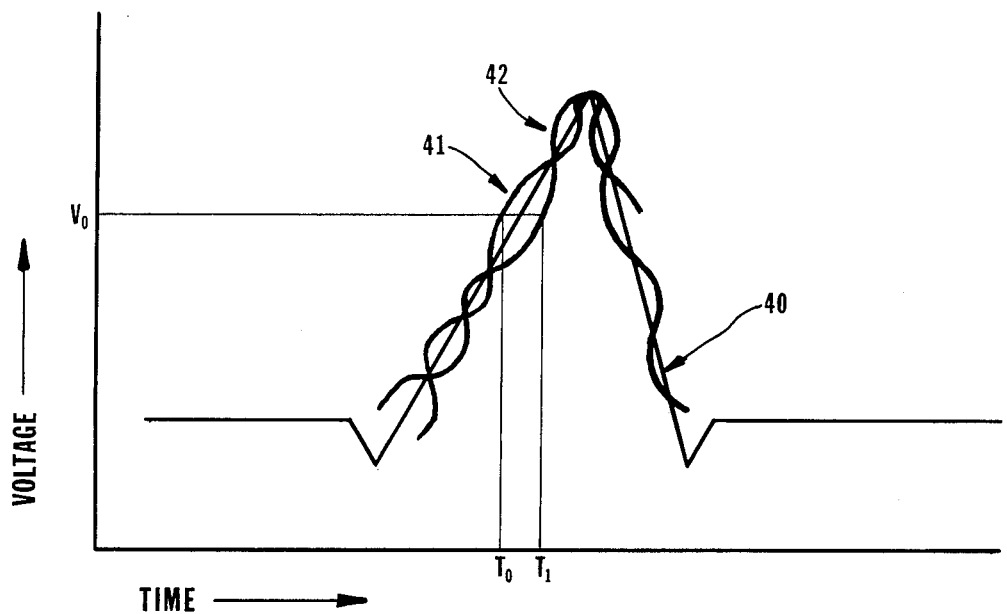
FIG. 3 is a diagram of three superimposed waveforms which demonstrate the problem associated with prior art methods of establishing an accurate synchronization time.

FIG. 3, which shows three waveforms 40, 41 and 42 superimposed upon one another, demonstrates the prior art problems in establishing a precise, reliable alignment time. Prior art methods derive a synchronization time by delineating a single, fixed threshold voltage (Vo) of such a magnitude that it is generally greater than that of floor or baseline noise yet still attainable by cycles of interest. The synchronization time (To) for the signal or signal cycle is the time (T) at which the single threshold voltage (Vo) is first attained by that signal or cycle. However, the synchronization time (To) derived by a single threshold voltage (Vo) is highly sensitive to additive signal noise present in the area of the theshold voltage.

Assuming that the waveforms 41 and 42 each represent alternative versions of the same fundamental waveform 40, which contain typical levels of additive noise, then the time coordinates (To) and (T1) are the corresponding threshold times yielded upon attainment of the single threshold voltage (Vo). Since the variance in voltage data points between the waveforms 41 and 42 is due solely to noise, the difference in threshold times To-T1 is also due solely to signal noise. This difference is termed time or phase jitter.

Applicants recognized that the error in synchronization time was related to timing variance or phase jitter and that synchronization time error could be quantified. The synchronization time error (E) associated with additive signal noise in the region of a single threshold voltage (Vo) is expressed as:

$$E(\text{time}) = \frac{E(\text{voltage})}{\left|\frac{dv}{dt}\right|}$$

where
E (time)=error in time,
E (voltage)=noise, and $$\frac{dv}{dt}$$

=the slew rate of the signal.

Figure 4:
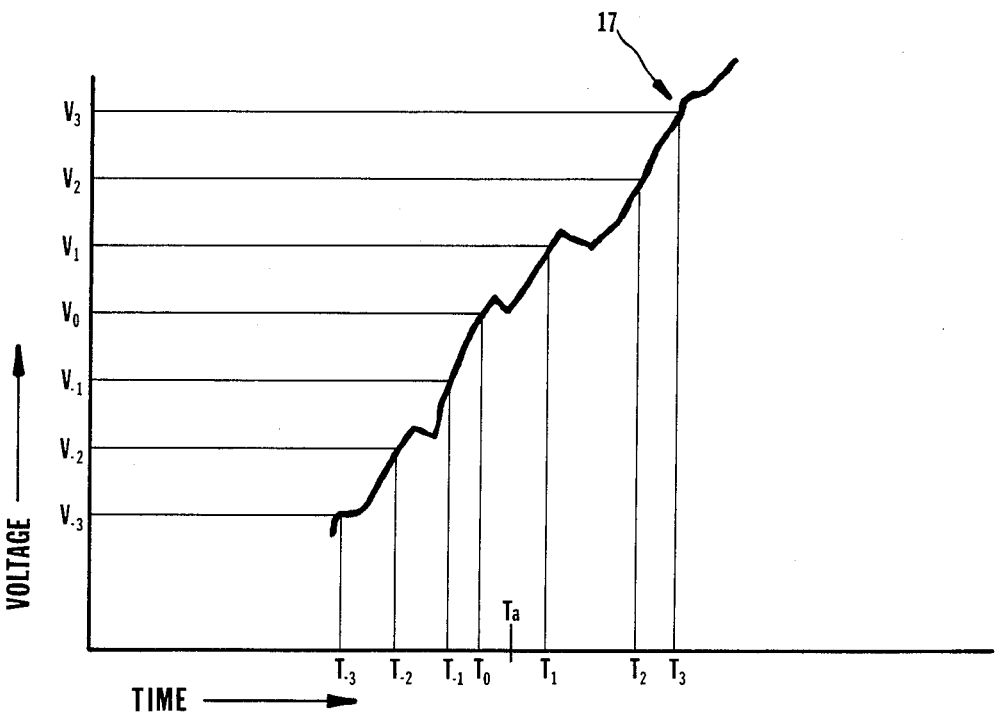
FIG. 4 is an expanded view of the threshold region of the first R-wave shown in FIG. 1.

Referring to FIG. 4, Applicants also recognized that synchronization time error is reduceable by utilizing multiple threshold voltages (Vx) to yield multiple synchronization times (T−1 to +1). Subsequent averaging of these multiple synchronization times (Tx) yields an accurate alignment time (Ta). The synchronization time error associated with the dependence on any single time coordinate (Tx) will be shown below to be significantly reduced by this method.

In accordance with the present invention, the terrain biased dynamic multiple threshold synchronization method yields an accurate, reliable alignment time for each electrocardiographic cycle 12, 13, 14 and 15 shown in FIG. 1, from which to align it with other cycles. The first step in the process involves delineating a plurality of threshold voltages or points which are discrete, instantaneous voltage levels. A predetermined number of threshold points are set. The multiple threshold points are set so that they correspond to a high amplitude edge on the positive or the negative slope of the R-waves or both simultaneously. Although it contains additive signal noise, this portion is relatively invariant and predictable in comparison with lower amplitude areas which are subject to high levels of additive floor noise, and, therefore, provides a relatively reliable position from which to establish a reference point. Such a position also coincides with a major underlying periodic physical phenomenon, the contraction of the heart. The near-peak portion of the R-wave selected must be below the peak amplitude so as to minimize the elimination of a cycle. For non-ECG signals, the exact positioning of the threshold points is a function of the particular channel response and pulse characteristics of the system.

Multiplicative noise causes anomolous or low amplitude ECG cycles 13, as shown in FIG. 1. Such cycles may fall below threshold voltages which are set in a fixed position. Therefore, the thresholds are preferably set in relative positions based on the peak voltage of each cycle 12, 13, 14 and 15 for which an alignment time is being established. This positioning technique is dynamic in that a new, local set of threshold points is established for each cycle. In this manner, it is assured that alignment references are established for all cycles, including the low amplitude cycle 13 which results from multiplicative noise and which would otherwise remain unsynchronized.

The first step in relative or dynamic threshold positioning consists of determining the peak voltage of each cycle. The threshold points derived in the multiple thresholding technique are then set as predetermined percentages of each calculated peak voltage to yield a set of local thresholds for each cycle. For electrocardiographic signals, thresholds in the region of from 60-80% of the peak voltage have been found to be desirable for this purpose. The dynamic positioning technique is usable with the prior art single threshold technique, as well as with the multiple thresholding method of this invention.

As was previously discussed, DC shifts cause signal baseline wandering as shown in cycle 15 of FIG. 1. These signal fluctuations cause errors in the time attainment of threshold points (either fixed or dynamic). The effects of a wandering baseline are compensated for by adjusting the dynamic threshold positioning steps based on the signal terrain. Utilizing the preferred dynamic multiple thresholds and with particular reference to cycle 15, the first step in threshold positioning involves determining the actual baseline for each cycle. The actual baseline is the true baseline voltage of the cycle as opposed to the expected baseline voltage based either on a zero voltage or on an average baseline calculated over a larger portion of the signal. The actual baseline voltage is calculated on an isoelectric portion 19 when one exists or over a plurality of instantaneous near-baseline points on the cycle when one does not exist.

Next, the peak voltage of each cycle is determined. The actual baseline is then subtracted from the peak voltage to yield a relative peak voltage value. Local multiple thresholds for each cycle are then determined by the dynamic threshold positioning steps discussed above, based on the relative peak value. Finally, the actual baseline is added to each local threshold to yield a set of adjusted local thresholds for each cycle. These steps bias each dynamic threshold based on the baseline shift. The biased threshold voltages for each cycle relate directly to voltage variables corresponding to the signals underlying physical phenomena and are independent of DC shifts. The terrain biasing technique is also usable with the single threshold determination technique and/or the fixed threshold positioning technique of the prior art.

The next step of the synchronization method is to calculate a set of sample times (Tx) for each cycle 12, 13, 14 and 15. Sample times are the times at which each adjusted local threshold (Vx) is attained by the cycle. Following this determination, the sample times (Tx) are averaged to yield a mean threshold time or alignment time (Ta) in accordance with the equation:

$$Ta = \frac{1}{n} \sum_{o}^{n-1} Tx$$

where n is the number of threshold points taken.

Preferably, a weighing criteria is utilized in averaging the sample times (Tx). Weighing factors are assigned to each sample time according to its relative position in the set of observed sample times; for example, sample times corresponding to median thresholds receive a relatively higher weighing factor than those corresponding to thresholds disposed toward the high and low limits of the set of thresholds. A weighted alignment time (Taw) is derived by multiplying each sample time (Tx) by its particular weighing factor, summing the products, and dividing by the total number of sample times.

The terrain biased dynamic multiple threshold synchronization method reduces the deleterious effects of additive signal noise in establishing a precise time domain reference point for alignment of different cycles or for synchronization of an individual cycle or the entire signal with another heterogeneous signal or cycle thereof. The method provides multiple thresholds as opposed to a single threshold point for testing the voltage attainment of the signal with respect to time. The multiple threshold voltages yield a corresponding plurality of time coordinates from which a mean time is derived, as opposed to a single, noise sensitive time reference. The method also reduces the negative effects of multiplicative signal noise by providing dynamic or relative thresholds as opposed to fixed-position thresholds. In the method, local thresholds are set as a function of each individual cycle as opposed to the overall signal. In this way low amplitude cycles, such as cycle 13 in FIG. 1, are tested for threshold voltage attainment even if they have an amplitude below the local threshold levels of surrounding higher amplitude cycles. The method also reduces the negative effects of wandering baselines, such as that exhibited by cycle 15, by biasing for differences in voltage between baselines of successive cycles. In this manner an adjusted voltage threshold is established for each cycle, based on its actual baseline.

The weighted mean alignment time (Taw) derived by the above-described method is utilized to synchronize the successive waveforms 12, 13, 14 and 15. This involves aligning the weighted mean alignment times for each cycle with one another to provide a time scale relationship. Such alignment establishes a relative time scale for representing the voltage variables of the individual cycles that is common to all cycles.

The cycles synchronized by the above-described method may then be displayed or averaged. The first step in the signal averaging process involves detecting and identifying a predetermined number of cycles 12, 13, 14 and 15 of the overall signal waveform 10. The exact number of cycle samples required is dependent upon the number of samples that constitutes a statistically significant population. This is calculated generally by:

$$\text{number of samples} = \left( \frac{\text{desired } \frac{S}{N} \text{ ratio}}{\text{actual } \frac{S}{N} \text{ ratio}} \right)$$

The next step in averaging involves the addition of the voltage variables from each cycle for each relative time position and dividing by the total number of cycle samples. This step yields a mean instantaneous voltage for each time position. Averaging is repeated for each relative time position to yield the waveform 11, shown in FIG. 2. It represents the mean cardiac voltage as a function of relative time.

Figure 5:
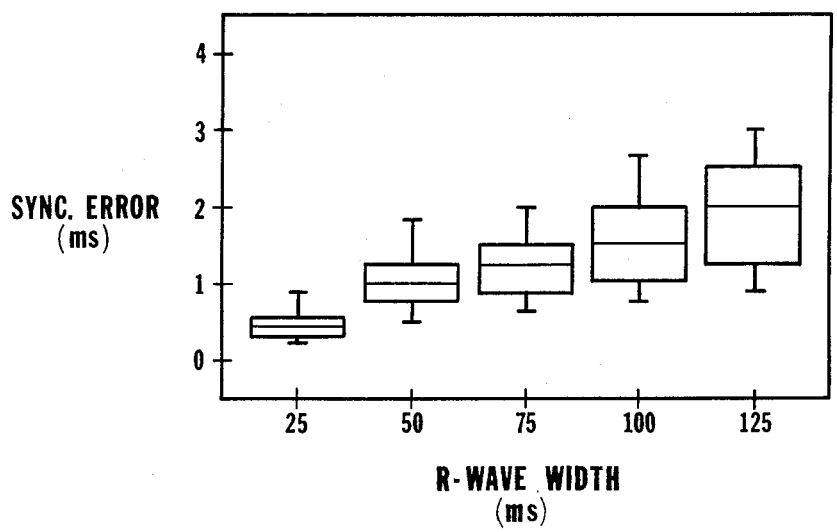
FIG. 5 is a graph plotting synchronization error versus R-wave width for computer averaged signals synchronized without the multiple threshold technique.
Figure 6:
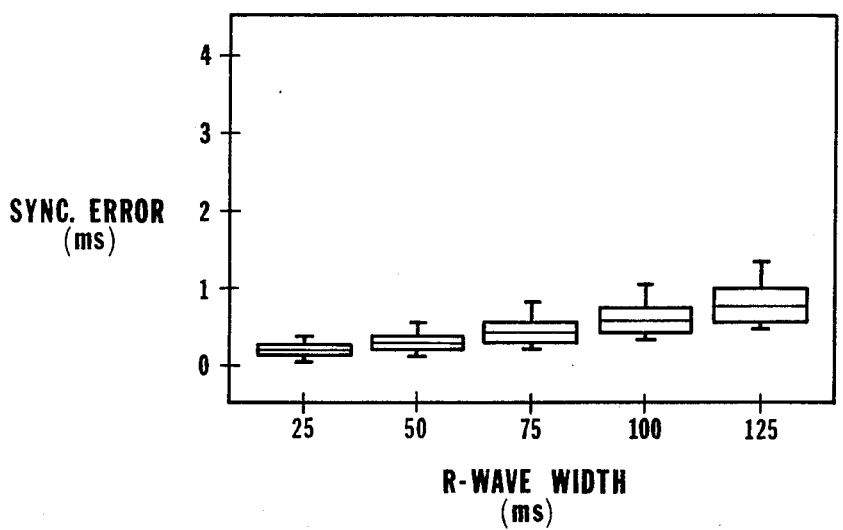
FIG. 6 is a graph plotting synchronization error versus R-wave width for computer averaged signals synchronized with the multiple threshold technique.

FIG. 5 shows a bar graph of synchronization error versus R-wave width for a computer simulated synchronization of input electrocardiographic signals having typical levels of 60 Hz and white noise, wherein the multiple threshold synchronization method of this invention was not utilized. FIG. 6 shows a graph of synchronization error versus R-wave width for a computer simulated synchronization of input electrocardiographic signals having typical levels of 60 Hz and white noise, wherein the multiple threshold method of this invention was applied. A comparison of the results depicted in the above-mentioned graphs illustrate the significant reduction in the synchronization error when the signals were synchronized utilizing multiple thresholds.

Figure 7:
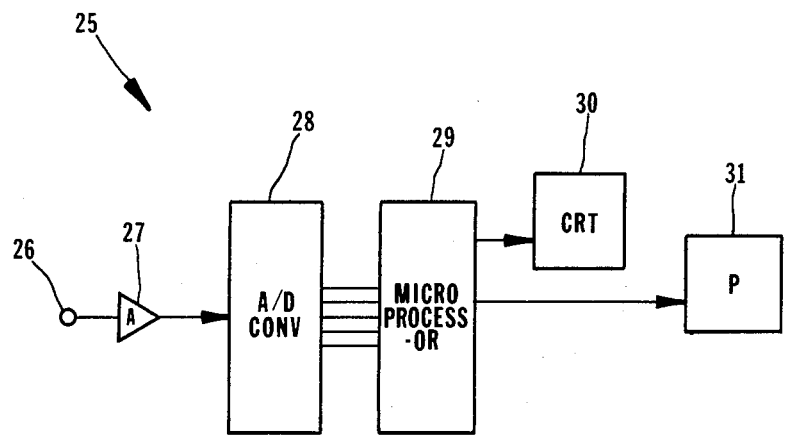
FIG. 7 is a schematic representation of an embodiment of the device of the present invention.

FIG. 7 shows an embodiment of the device 25 of the present invention. The device 25 is used to synchronize and average periodic electrocardiographic signals to eliminate the effects of noise for improved diagnosis. The device 25 comprises a microprocessor 29, a preamplifier 27, an analog to digital converter 28, a cathode-ray tube (CRT) 30 and a printer 31. The device 25 is usable with other electro-medical apparatus for further analysis of the electrocardiographic signals. Additionally, other types of electrical, acoustical and/or electromagnetic signals, including non-periodic signals, may be synchronized for other purposes utilizing this and other embodiments of the device 25.

A periodic signal received at an electrode 26 is amplified by means of the pre-amplifier 27 which produces an electrical analog signal which is a function of the input signal. The output signal is inputted, via the analog to digital converter 28, to the microprocessor 29. The microprocessor 29 is programmed to perform the previously described terrain biased dynamic multiple threshold synchronization method and the averaging method on the digitized output signal from the converter 28.

Figure 9:
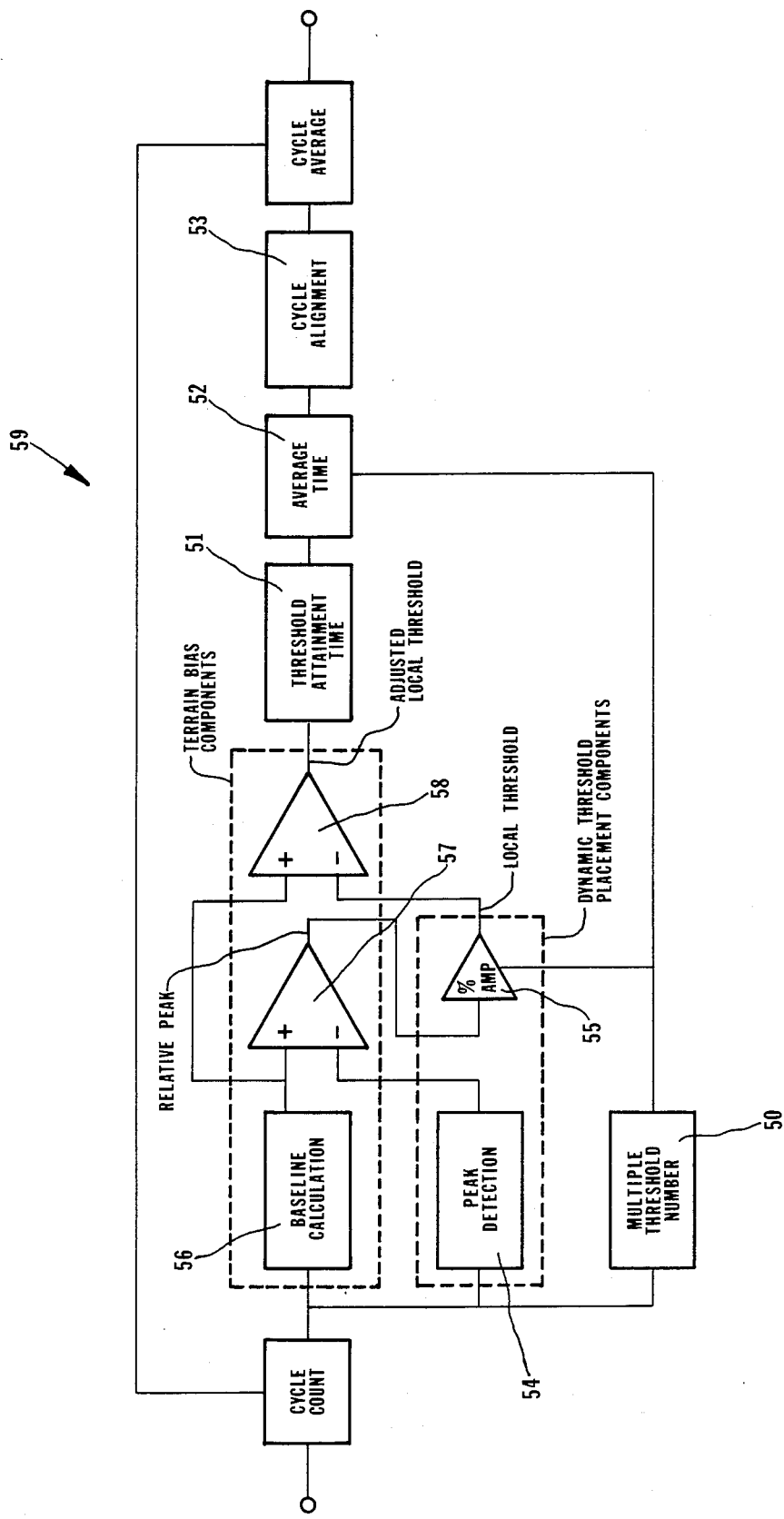
FIG. 9 is a schematic flow diagram of the method of this invention with respect to the system utilized to perform this method.

Referring to FIG. 9, the programmed microprocessor 29 provides a control system 59 to perform the process steps of this invention. It first determines a predetermined number of threshold points. The multiple threshold points are discrete voltage levels set for each individual signal cycle. Next the actual baseline of each cycle is calculated, preferably over an isoelectric region. The control system 59 then determines the peak voltage of each cycle. It then subtracts the actual baseline from the peak voltage yielding a relative peak voltage. The multiple threshold points are then positioned as percentages of the relative peak voltage yielding a set of local threshold points for each cycle. Finally, the position of each local threshold point is adjusted by adding the actual baseline of the cycle to yield a set of adjusted local voltage threshold points.

The control system 59 next calculates the time at which each adjusted local threshold point is attained by the cycle being analyzed. Each observed time coordinate pertaining to the particular cycle is then summed and divided by the total number of threshold attainment times to yield a mean threshold attainment time or alignment time. Preferably, the control system 59 assigns each observed sample threshold time a weighing factor prior to averaging to yield weighted mean threshold times. This is accomplished by utilizing a digital filter of a type known in the art to generate weighting criteria in conjunction with mean threshold time determination.

The weighted mean threshold times are utilized as a common reference point from which to align each cycle. The control system 59 aligns each cycle with respect to the weighted means threshold time, thus shifting all signal data of each cycle. Such alignment establishes a relative time scale for representing the voltage variables of the individual cycles. On the relative time scale, voltage similarities and dissimilarities between successive cycle samples correspond with one another and may now be accurately compared.

Corresponding voltage data points on each cycle are next averaged in the microprocessor 29 yield a composite signal. For each relative time position, the voltage variable from each cycle are summed and divided by the total number of cycles sampled to derive a mean voltage. The microprocessor 29 repeats this process for each relative time position to yield a composite waveform representing the mean cardiac voltage as a function of relative time, as shown and discussed with respect to FIG. 2.

The method described above with respect to the microprocessor 29, therefore, utilizes the control system 59 to perform the terrain biased dynamic threshold synchronization and averaging method. As further shown in FIG. 9, the system 59 is comprised of means 50 to select a plurality of discrete or separate threshold voltages, means 51 to detect the times at which these threshold voltages are attained, means 52 to determine the average threshold times and means 53 to align the signals based on the average threshold times. Additionally, shown in FIG. 9, the system 59 preferably includes means 54 to determine the peak amplitudes of the signals, means 55 to set the threshold voltages as a percentage of the peak amplitude, means 56 to determine the actual baseline voltages of the signals, means 57 to subtract baseline voltages from the peak amplitudes and means 58 to add the baseline voltages to the threshold voltages. These means discussed with respect to FIG. 9 can be conventional hardware components or software systems.

The composite signal is an accurate mean representation of all the signals actually received by the device 25. The composite signal greatly diminishes the effects of noise in the individual signals. The composite signal is transferred from the microprocessor 29 to the cathode-ray tube 30 and/or to the printer 31, allowing the operator to visualize the improved representation of electrocardiographic function. Alternatively, the signal may be further analyzed by other electro-medical devices.

Figure 8:
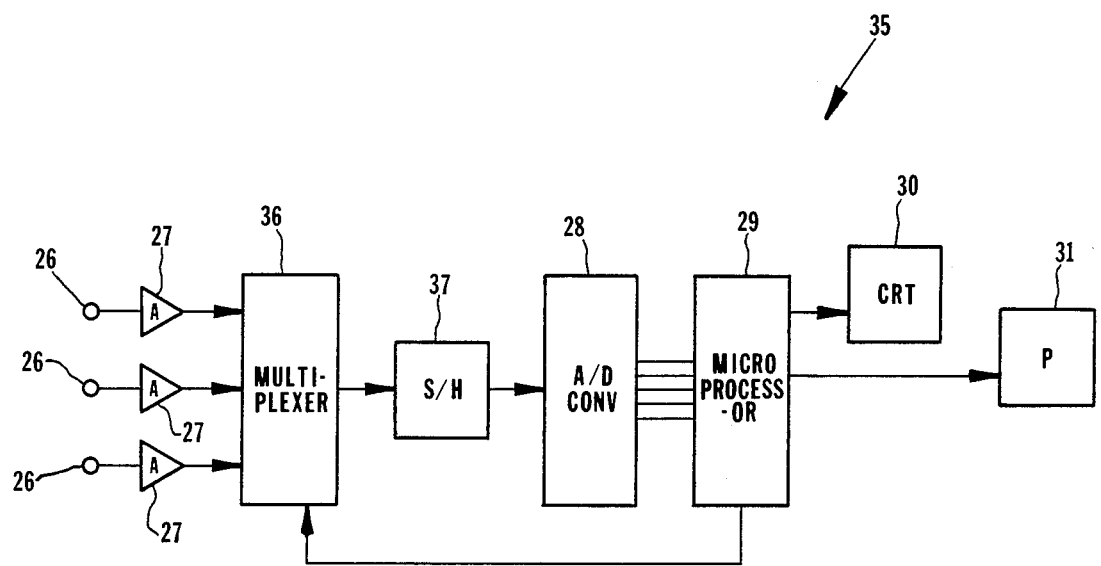
FIG. 8 is a schematic diagram of another embodiment of the device of the present invention.

FIG. 8 shows another device 35 of the present invention. It has individual pre-amplifiers 27 connected to a plurality of electrodes 26. The amplified signals from the pre-amplifiers 27 are inputted to a multiplexer 36 which is connected both to the analog to digital converter 28 through a sample and hold circuit 37 and to the microprocessor 29.

As many changes are possible to the embodiments of this invention utilizing the teachings thereof, the descriptions above, and the accompanying drawings should be interpreted in the illustrative and not the limited sense.

That which is claimed is:

1. A method of establishing an accurate synchronization point for a signal comprising the steps of:
   a. detecting a signal;
   b. selecting a plurality of voltage thresholds generally incrementally spaced and corresponding to the signal;
   c. detecting a time at which each said threshold is attained by the signal; and
   d. calculating a mean time at which said thresholds are attained by the signal, whereby said mean time is used to synchronize the signal with other signals.

2. The method of claim 1, additionally comprising the step of determining a peak amplitude of the signal and wherein said thresholds are selected as percentages of said peak amplitude.

3. The method of claim 1, additionally comprising the steps of determining an actual baseline of the signal and adding said baseline to each said threshold to adjust said thresholds for DC shifts prior to step (c).

4. The method of claim 3, wherein said actual baseline is calculated over an isoelectric region of the signal.

5. The method of claim 3, wherein said actual baseline is calculated as an average over an extended portion of the signal.

6. The method of claim 1, wherein said threshold times are accorded weighing factors prior to calculating said mean time, each said time weighing factor being dependent upon its position relative to other said threshold times.

7. The method of claim 1, wherein the signal detected is an electrocardiographic signal having a plurality of cycles and wherein said steps (b), (c) and (d) are applied to each cycle to synchronize the cycles for their subsequent averaging.

8. The method of establishing accurate synchronization points for periodic electrical, acoustic and electromagnetic signals comprising the steps of:
   a. detecting input signal cycles;
   b. converting each input signal cycle into an output digital signal, said output digital signals being a function of the input signal cycles;
   c. selecting a plurality of discrete threshold voltage points, said threshold points generally corresponding to a predetermined range of near-peak voltages of said output digital signals;
   d. determining threshold times at which said threshold voltage points are attained by each said output digital signal;
   e. calculating an average threshold time for each said output digital signal; and
   f. synchronizing said output digital signal cycles based on said average threshold times, said synchronizing further having the steps of establishing a relative time scale for representing the voltage variables of each said output digital signal cycles based on said average threshold times and aligning said relative time scales with respect to their average threshold times.

9. The method of claim 8, additionally comprising the step of determining the peak amplitude of each said output digital signal and wherein said threshold voltage points are selected as percentages of said peak amplitude.

10. The method of claim 8, additionally comprising the steps of determining an actual baseline voltage of each said output digital signal and adding said baseline voltage to each said threshold voltage point to adjust said threshold voltage points for DC shifts prior to step (d).

11. The method of claim 8, wherein said threshold times are accorded weighing factors prior to calculating said average threshold time, each said time weighing factor being dependent upon its position relative to other said threshold times.

12. A method of averaging periodic electric, acoustic and electromagnetic signals comprising the steps of:
  a. detecting an input signal to be averaged;
  b. converting a predetermined number of input signal cycles into output digital signals, said output digital signals being a function of the input signal cycles;
  c. synchronizing said output digital signals, said synchronization comprising the steps of:
    i. determining an actual baseline voltage of each said output digital signal;
    ii. determining a peak amplitude of each said output digital signal;
    iii. subtracting said actual baseline voltage from said peak amplitude to yield a relative peak amplitude for each said output digital signal;
    iv. calculating a plurality of threshold voltage points for each said output digital signal, said points corresponding to a percentage of said relative peak amplitude;
    v. adding said actual baseline voltage to each said threshold voltage point to yield adjusted threshold voltage points for each said output digital signal;
    vi. determining threshold times at which said adjusted threshold voltage points are attained by each said output digital signal;
    vii. providing a weighing factor to each said threshold time for each said output digital signal, each said weighing factor being dependent upon its position relative to other said threshold times;
    viii. calculating an average threshold time for each said output digital signal; and
    ix. aligning said output digital signal cycles based on said average threshold times, said alignment further comprising the step of establishing a relative time scale for each said output digital signal based on said average threshold times;
  d. summing the voltage data points of each said synchronized signal at each position on said relative time scale; and
  e. dividing the sum of step (d) by said predetermined number of input signal cycles.

13. In combination with a method of synchronizing electrical signals, of a type wherein a threshold voltage is established and a time at which said threshold voltage is attained by the electrical signal is utilized as an alignment reference, the improvement which comprises:
  a. selecting a predetermined number of additional threshold voltages in the general region of the threshold voltage;
  b. detecting the times at which said threshold voltages are attained by the electrical signal; and
  c. determining a mean time in (b), whereby said mean time is utilized as a more accurate synchronization reference which is less sensitive to signal noise in said general region of the threshold voltage.

14. The improved method of claim 13, additionally and initially comprising the step of determining a peak amplitude of the signal and wherein the position of said threshold voltage is adjusted to conform to a percentage of said peak amplitude.

15. The improved method of claim 13, additionally comprising the steps of determining an actual baseline voltage of the signal and adding said baseline voltage to the threshold voltages prior to step (b) to adjust said voltage thresholds for DC shifts.

16. The improved method of claim 13, wherein said threshold times are accorded weighing factors prior to calculating said mean time, each said time weighing factor being dependent upon its position relative to other said threshold times.

17. In an electrical signal synchronizing system including a CPU and input/output devices, a control section for operating said system comprising:
  a. means for selecting a plurality of discrete threshold voltages, said threshold voltages generally corresponding to signals of interest;
  b. means for comparing signals with said threshold voltages and for detecting times at which said threshold voltages are attained by the signals;
  c. means for determining an average threshold times for the signals; and
  d. means for aligning signals based on said average threshold times.

18. The control section of claim 17, additionally comprising means for determining a peak amplitude of signals and wherein said threshold voltage selection means selects said threshold voltages as percentages of said peak amplitudes.

19. The control section of claim 17, additionally comprising means for determining the actual baseline voltages of signals and means for adding said baseline voltages to said threshold voltages to adjust said threshold voltages for DC shifts.

20. The control section of claim 17, additionally comprising filter means for according weighing factors to said threshold times, each said weighing factor being dependent upon its relative position in the set of said threshold times.

21. In a device for automatically averaging periodic electrical, acoustic and electromagnetic signals, a system for synchronizing of signal cycles with respect to time comprising:
  a. means for converting a predetermined number of input signal cycles into output digital signals, said output digital signals being a function of the input signal cycles;
  b. means for determining an actual baseline voltage of each said output digital signal;
  c. means for determining a peak amplitude of each said output digital signal;
  d. means for subtracting said actual baseline voltage from said peak amplitude to yield a relative peak amplitude for each said output digital signal;

e. means for calculating a plurality of threshold voltage points, said points corresponding to a percentage of said relative peak amplitude for each said output digital signal;
f. means for adding said actual baseline voltage to each said threshold voltage point to yield adjusted threshold voltage points for each said output digital signal;
g. means for determining threshold times at which said adjusted threshold voltage points are attained by each said output digital signal;

h. digital filter means for providing a weighing factor to each said threshold time, each said weighing factor being dependent upon its position relative to other said threshold times; for each said output digital signal;
i. means for calculating an average threshold time for each said output digital signal; and
j. means for aligning said output digital signal cycles based on said average threshold times, said means establishing a relative time scale for each said output digital signal based on said average threshold times.

* * * * *